United States Patent [19]
Baker et al.

[11] Patent Number: 4,582,704
[45] Date of Patent: Apr. 15, 1986

[54] CONTROL OF BEAN RUST WITH *BACILLUS SUBTILIS*

[75] Inventors: Con J. Baker, Columbia; J. Rennie Stavely, Silver Spring, both of Md.

[73] Assignee: The United States of America as represented by the Secretary of Agriculture, Washington, D.C.

[21] Appl. No.: 539,907

[22] Filed: Oct. 7, 1983

[51] Int. Cl.[4] .................. A61K 37/00; C12N 1/20; C12R 1/125
[52] U.S. Cl. .................... 424/93; 435/253; 435/839
[58] Field of Search ................ 435/253; 424/93

[56] References Cited
PUBLICATIONS

Phytopathology vol. 71 p. 777 (1981), Greenhouse Control of Bean Rust with *Bacillus subtilis*.
Phytopathology vol. 72, p. 986 (1982) Characterization of the Component Produced by *Bacillus subtilis* which Inhibits Bean Rust.
Plant Disease Reporter vol. 61, pp. 543–545, (1977).

*Primary Examiner*—Lionel M. Shapiro
*Attorney, Agent, or Firm*—M. Howard Silverstein; William E. Scott; David G. McConnell

[57] ABSTRACT

A strain of *Bacillus subtilis* designated APPL-1 and a purified extract of APPL-1 were found to effectively control and inhibit rust on bean plants.

3 Claims, No Drawings

CONTROL OF BEAN RUST WITH *BACILLUS SUBTILIS*

BACKGROUND OF THE INVENTION

1. Field of The Invention

This invention relates to the use of a particular isolate of *Bacillus subtilis* to control or to inhibit the development of rust on bean plants and other agricultural products. It also pertains to the use of a certain fraction obtained from purifying the isolate of *B. subtilis* for inhibiting the development of rust.

2. Description of The Art

The use of species of Bacillus as antagonists of plant pathogens in the phyllosphere is well known. *Bacillus cereus* subsp. *mycoides* has been found to control brown spot on tobacco leaves. Cereal rust has been controlled by spray treatment of wheat and oats with *B. pumilus*. The strain of *B. subtilis* used in this invention was found to suppress charcoal rot of potato, Plant Dis. Reptr. 61, 543-546, 1977.

SUMMARY OF THE INVENTION

An object of this invention is to provide a method for controlling or inhibiting the development of rust on beans and other agricultural products such as wheat that is safe for the growers and consumers of these agricultural products.

Another object is to provide a method for controlling rust which is effective on major varieties of dry and snap beans.

Still another object is to provide a method and an agent that is effective against major races of the highly variable pathogen, rust.

Another object is to provide a method and agent for controlling rust that is economical to use.

A further object is to reduce the need for breeding disease resistant lines of plants and for reducing the need to continually test these disease resistant lines.

A still further object is to increase the production of beans and other agricultural products by greatly reducing the losses that are caused by rust.

Another further object is to provide a means of improving the environment by reducing the need to use synthetic fungicides.

According to this invention the above objects are accomplished by treating bean plants and other agricultural plants with a particular strain of *Bacillus subtilis* designated as APPL.-1. The objects are also accomplished by treating the plants with an easily obtainable heat stable culture-extract obtained from the biocontrol agent APPL-1. Both APPL-1 and the culture-extract are applied as a spray or as an aerosol.

A viable culture of the strain of *B. subtilis* designated as *Bacillus subtilis* APPL-1 has been deposited with the Culture Collection at the Northern Regional Research Center, United States Department of Agriculture, Peoria, Illinois, 61604, and its accession number is NRRL B-15570. With reference to 886 O.G. 638, progeny of this strain will be available during pendency of the patent application to one determined by the Commissioner of Patents and Trademarks to be entitled thereto under 37 CFR 1.14 and 35 USC 122. All restrictions on the availability of progeny of the strain to the public will be irrevocably removed upon the granting of the patent of which the strain is the subject.

DESCRIPTION OF THE INVENTION

Rust is a major agricultural problem in the United States and bean rust, caused by *Uromyces phaseoli*, is a very major disease problem of dry and snap beans in the United States which causes very high yield and monetary losses. Synthetic fungicides, principally Manzate, a dithiocarbamate, aid in controlling bean rust, but are expensive, not completely effective, and undesirable because of possible toxic side effects to the environment and to man. Alternatives to present day pesticides are urgently needed in all phases of pest control and this is especially true for bean rust, nationwide as well as worldwide. Use of synthetic fugicides to control bear rust is widespread on fresh market and processing snap beans as well as on pinto, navy, and other dry beans. Breeding for resistance is a major effort because of the need to reduce dependence on synthetic fungicides. However, because of the highly variable nature of the pathogen causing the disease and the wide variety of geographical areas where beans are grown, this breeding program requires maximal and continual input of time, effort and resources worldwide. The present invention provides a new and different means for inhibiting the development of and therefore controlling all major races of the bean rust pathogen.

In order to develop the present invention we maintained a number of bacterial cultures on nutrient agar at 25° C. One of them was a cluture of *Bacillus subtilis* designated APPL-1. Another was a culture of *Bacillus subtilis* designated APPL-2, which was isolated from an entirely different soil than that from which APPL-1 was isolated. Other cultures were *B. cereus* subsp. *mycoides* isolate B 23, which controls lesion production on tobacco caused by *Alternaria alternata*, an isolate of *B. thuringiensis* HD-1, a culture of *Erwinia ananas* pv. *uredovora*, and an isolate of *Pseudomonas syringae* which is avirulent on beans. Each of the above bacterial species was transferred from nutrient agar to one liter of Eugon broth in a 2.8 liter fernbach flask. Eugon broth consists of the following ingredients: tryptose, 15 gm; Soytone, an enzymatic hydrolysate of soybean meal, 5 gm; dextrose, 5 gm; cystine, 0.2 gm; sodium chloride, 4 gm; sodium sulfite, 0.2 gm; sodium citrate, 1.0 gm. Other equivalent medium or broth may be used in place of Eugon broth. The cultures were incubated on a circulatory shaker at 25 rpm at 30° C. and in the dark until early stationary phase. Culture supernatant and other culture fractions tested for rust inhibition activity were applied to young plants of *Phaseolus vulgaris* cv. Lake Shasta with primary leaves one-fifth to one-third expanded. Five seeds were planted per four inch plastic pot, germinated in a greenhouse at 24° to 30° C., and thinned to three uniform plants per pot, five to seven days after seeding. The bacterial suspensions and test solutions were then sprayed onto the plants with a spray device from a distance of approximately 12 to 15 inches to give thorough coverage of all above ground plant surfaces. The plants were then allowed to dry.

Urediospores of *Uromyces phaseoli* were added to a solution of distilled water containing 0.01% Tween 20 and stirred on a magnetic stirrer for about five minutes. Any wetting agent similar to Tween 20 may be used in its place. Urediospore concentration was determined with a hemocytometer and adjusted to about 20,000 spores per ml. This suspension was lightly sprayed onto the upper surface of leaves of plants pretreated or nontreated with the bacterial suspensions. After the film dried, the plants were placed overnight in a dew chamber in which the relative humidity was 100% and the air temperature was 22° C. The plants were moved to a greenhouse the next morning. In eight to fourteen days uredial pustules had developed and were counted. All of these in vivo treatments were applied to at least ten replicate plants.

As noted in Table 1, Lake Shasta bean plants pretreated with the cultures of B. subtilis, B. cereus subsp. mycoides, B. thuringiensis and E. ananas pv. uredovora and then sprayed with urediospores from U. phaseoli collection 73-16 had 80 to 99% fewer uredial pustules than those pretreated with avirulent P. syringae or sterile Eugon broth or given no treatment. The bacterial isolate most inhibitory to rust development was B. subtilis APPL-1, which consistently reduced the number of pustules by more than 90% as compared to the nontreated control. This is a significantly greater reduction than that obtained by treatment with APPL-2 or the other effective bacteria. There is no significant difference among the percent reduction in pustule numbers caused by B. subtilis APPL-2, B. cereus subsp. mycoides, B. thuringiensis or E. ananas pv. uredovora.

In order to determine if a culture of B. subtilis APPL-1 in early stationary phase was broadly effective, its effect on rust development on five bean cultivars was determined. The pathotype of U. phaseoli used in this experiment was rust collection 75-22. The cultivars tested included Lake Shasta, Mount Hood, Pinto 111, Mountaineer White Half-Runner, and BBL 47. All five cultivars are susceptible to rust collection 75-22. As noted in Table 2 a 96% to 98% reduction occurred in the number of pustules produced by rust collection 75-22 on all five cultivars.

The effect of a culture of B. subtilis APPL-1 in early stationary phase on symptom development on bean cv. Lake Shasta innoculated with five pathogenically unique collections of U. phaseoli was also determined. The bean cultivar was sprayed with the culture of APPL-1 and then innoculated with the five unique pathotypes of U. phaseoli. As seen in Table 3 there was no statistical difference among the five pathotypes of U. phaseoli. The reduction in number of necrotic spots caused by rust collection 73-23 on B. subtilis APPL-1 pretreated Lake Shasta did not significantly differ from the effects of pretreatment on the number of pustules that were produced by collections 79-4, 73-16, 75-22, and 73-32. Eleven additional collections of rust that contain unique pathotypes different from those listed in Table 3 were also tested and the B. subtilis APPL-1 pretreatment had an identical inhibitory effect on development of either the necrotic or pustule reaction, whichever was characteristic of the appropriate host-pathotype combination. The eleven addition collections of rust are 79-15F, 79-6-1, 79-6A-1, 79-6C-1, 79-15B-1, 79-15G-1, 79-15A-1, 79-4B-1, 81-10A-1, 79-15A-4, and 81-IOA-3-1.

We found that cultures which are in late stationary phase contain substantially more inhibitor than cultures in early stationary phase. We have also found that the activity of culture filtrates can be stabilized by autoclaving for 20 minutes. Autoclaving does not greatly effect the inhibitor, but appears to inactivate degradative enzymes which are also present in these filtrates.

A high molecular weight fraction or extract is obtained by removing with centrifugation the bacterial cells from a culture of B. subtilis APPL-1, in late stationary phase, processing the supernatant through molecular filtration and retaining only the high molecular weight portion, that is, the portion greater than 100,000 daltons. This purified and concentrated extract controls bean rust at levels of less than one part per million.

A more definitive description of the preparation of the high molecular weight fraction is as follows:
1. Prepare and sterilize one liter of Eugon broth in a 2.8 l. fernbach flask.
2. Inoculate medium with loopful of APPL-1 from a 24 hour-old culture grown on a nutrient agar plate at 30° C.
3. Incubate on a circulatory shaker at 125 rpm at 30° C. until the culture is in late stationary phase.
4. Separate bacterial cells from cultural broth by centrifugation at 8,000 rpm.
5. Autoclave the broth for 20 minutes.
6. Place the broth in an Amicon or equivalent ultrafiltration cell with a membrane of 100,000 molecular weight cut-off. Apply pressure of about 20 p.s.i. until the liquid is reduced to somewhat greater than 200 ml.
7. Wash the retained high molecular weight fraction by twice adding a volume of water to the cell and applying pressure until the volume is reduced to 200 ml.

For larger scale operations, the following procedure may be used:
1. Prepare and sterilize 15 liter of Eugon broth in a 20 l Nalgene or equivalent carboy fitted with an air inlet tubing and 0.2 micron air filter.
2. Inoculate medium with 500 ml of 24 hour-old culture of APPL-1 grown on Eugon broth on a shaker at 125 rpm and 30° C.
3. Set air flow to agitate broth to insure mixing and allow air to exit through carboy cap. Continue until culture is in late stationary phase.
4. Separate bacterial cells from broth by microporus filtration through a Millipore or equivalent pellicle chamber using 0.2 micron filters.
5. Ultrafilter the supernatant from 4 using a 100,000 molecular weight cut-off membrane.
6. Wash the material retained on filter in step 5 twice with distilled water and reduce the volume to 3 liters.

Field tests using three replicates of one meter rows of beans have shown that B. subtilis APPL-1 cultures and culture extracts are quite effective in controlling bean rust. The treatments include: (1) water, and (2) Eugon broth as control treatments; (3) early stationary phase and (4) late stationary phase cultures of B. subtilis APPL-1; and (5) high molecular weight fraction of a late stationary phase culture of B. subtilis APPL-1. As shown in Table 4, the B. subtilis APPL-1 cultures and the high molecular weight fraction reduced rust by about 70 to 84% on Pinto 111 and about 82% on Lake Shasta beans. The cultures and high molecular weight fraction were diluted with an equal volume of water and then spray or aerosol applied to the bean plants. When diluted, one volume of culture to five volumes of water, the cultures retained rust inhibiting activity. Approximately 500 ml of the diluted culture was used to treat about 75 bean plants.

Histological examination of the plant leaves was conducted by approved procedures. Leaves were removed from treated and control bean plants immediately after the plants were removed from the dew chamber. The leaves were sectioned with a scalpel into approximately one cm square pieces. The sections were immersed for 10 seconds in alcoholic lactophenol cotton blue modified to contain 0.1 g aniline blue per 40 ml. The sections were then rinsed briefly with 50% glycerin and mounted on a glass slide with cover slip for observation with an Olympus model BH-2 or equivalent light microscope. Leaf sections treated with *B. subtilis* had many nongerminated urediospores floating in the mounting solution. About 30% of the spores which remained on the leaf surface exhibited cytoplasm that had ballooned out but had remained attached to the spore cell wall. No normal germ tubes were observed on *B. subtilis* treated leaves. More than twice as many spores remained on the surface of the nontreated as on the treated leaves. Nearly 100% of the spores on the nontreated leaves had developed germ tubes 5 to 20 spore diameters in length during the overnight incubation.

TABLE 1

| Treatment | Uredial pustules/leaf Number (mean) | Control (%)[y] |
|---|---|---|
| *Bacillus subtilis* (APPL-1) | 0.5 ± .2 | 99[a] |
| *B. subtilis* (APPL-2) | 6.9 ± 1.0 | 84[b] |
| *B. cereus* subsp. *mycoides* | 9.2 ± 1.5 | 80[b] |
| *B. thuringiensis* | 6.9 ± 1.6 | 85[b] |
| *Erwinia ananas* pv. *uredovora* | 6.4 ± 1.0 | 86[b] |
| *Pseudomonas syringae* | 47.2 ± 7.1 | 0[c] |
| Untreated control | 45.3 ± 6.5 | 0[c] |
| Culture medium control | 45.7 ± 6.2 | 0[c] |

[y]Percent control or reduction in number of pustules as compared to the number on untreated plants. Any two figures followed by the same letter are not significantly different by Duncan's Multiple Range test at p = 0.05.

TABLE 2

| Bean CV | Number of uredial pustules/leaf[a] B. subtilis treated (mean) | Nontreated (mean) | Control[b] % |
|---|---|---|---|
| Lake Shasta | 9 ± 2.9 | 231 ± 24.3 | 96 |
| Mount Hood | 12 ± 4.4 | 317 ± 29.4 | 96 |
| Pinto 111 | 8 ± 2.9 | 346 ± 19.9 | 98 |
| Mountaineer White Half Runner | 8 ± 2.1 | 322 ± 27.6 | 98 |
| BBL 47 | 3 ± .6 | 159 ± 27.9 | 98 |

[a]The primary leaves of nine plants were counted and averaged for each treatment and control.
[b]Percent control or reduction in number of pustules as compared to the number on untreated plants.

TABLE 3

| Collection | Average No. Uredia/leaf Treated (mean) | Control (mean) | Control[b] % |
|---|---|---|---|
| 79-4 | 1.6 ± .5 | 39.1 ± 14.5 | 96 |
| 73-23[a] | 0.7 ± .37 | 14.5 ± 1.1 | 95 |
| 73-16 | 0.5 ± .2 | 14.7 ± 4.0 | 97 |
| 75-22 | 0.6 ± .19 | 26.8 ± 5.5 | 98 |
| 73-32 | 0.4 ± .21 | 12.0 ± 2.7 | 97 |

[a]Collection 73-23 causes necrotic spots without sporulation on cv Lake Shasta, therefore, necrotic spots were counted rather than uredia.
[b]Percent control or reduction in the number of pustules as compared to the number on untreated plants. There is no significant difference between these figures at either the 95 or 99% level of significance.

TABLE 4

| Treatment | Cultivar | Average percent rust |
|---|---|---|
| 1. Water Control | Pinto III | 95 |
|  | Lake Shasta | 40 |
| 2. Eugonbroth Control | Pinto III | 85 |
|  | Lake Shasta | 15 |
| 3. *B. Subtilis* APPL-1 Culture in early stationary phase | Pinto III | 22 |
|  | Lake Shasta | 7 |
| 4. *B. subtilis* APPL-1 Culture in late stationary phase | Pinto III | 15 |
|  | Lake Shasta | 7 |
| 5. *B. subtilis* APPL-1 High MW Fraction | Pinto III | 28 |
|  | Lake Shasta | 5 |

[a]Percent leaf area was estimated using the modified Cobb scale and the figures given are the averages from three replicates.
[b]Each treatment was applied on every Monday, Wednesday, and Friday for five weeks from time of seedling emergence.

We claim:

1. A method of controlling and inhibiting the development of rust on bean plants comprising applying to the plants an effective *Uromyces phaseoli* controlling amount of a late stationary phase culture of *Bacillus subtilis* APPL-1.

2. A method of preparing a purified extract of *Bacillus subtilis* APPL-1 comprising inoculating a suitable medium with a culture of *B. subtilis* APPL-1 in early stationary phase, incubating the inoculated medium until the culture is in late stationary phase, separating the bacterial cells from the culture, autoclaving the supernatant from the separation step, and ultrafiltering the supernatant to obtain that portion of the culture having a molecular weight greater than 100,000.

3. A method of inhibiting the development of rust on bean plants comprising applying to the plants an effective *Uromyces phaseoli* inhibiting amount of a high molecular weight culture of *Bacillus subtilis* APPL-1 prepared by the method of claim 2.

* * * * *